United States Patent
Akins, Jr.

(10) Patent No.: US 7,347,922 B2
(45) Date of Patent: Mar. 25, 2008

(54) MULTI-DIMENSIONAL PROTEOMIC ANALYSIS METHOD

(76) Inventor: Robert E. Akins, Jr., 15 Ridgewood Turn, Silverwood, Newark, DE (US) 19711

(*) Notice: Subject to any disclaimer, the term of this patent is extended or adjusted under 35 U.S.C. 154(b) by 214 days.

(21) Appl. No.: 10/107,812

(22) Filed: Mar. 28, 2002

(65) Prior Publication Data

US 2002/0153252 A1 Oct. 24, 2002

Related U.S. Application Data

(60) Provisional application No. 60/279,125, filed on Mar. 28, 2001.

(51) Int. Cl.
*G01N 27/26* (2006.01)
(52) U.S. Cl. .................. 204/456; 204/606; 204/461
(58) Field of Classification Search ........ 204/456–470, 204/606–621
See application file for complete search history.

(56) References Cited

U.S. PATENT DOCUMENTS

| | | | | |
|---|---|---|---|---|
| 4,735,697 A | * | 4/1988 | Burton | 210/656 |
| 5,164,055 A | * | 11/1992 | Dubrow | 204/455 |
| 5,275,708 A | * | 1/1994 | Akins et al. | 204/468 |
| 5,773,645 A | * | 6/1998 | Hochstrasser | 204/456 |
| 5,843,673 A | * | 12/1998 | Sharpe-Timms | 435/7.1 |
| 5,872,230 A | * | 2/1999 | Stocco et al. | 536/22.1 |
| 5,993,627 A | * | 11/1999 | Anderson et al. | 204/456 |
| 6,379,970 B1 | * | 4/2002 | Liebler et al. | 436/86 |
| 6,537,432 B1 | * | 3/2003 | Schneider et al. | 204/450 |

OTHER PUBLICATIONS

H. Sun et al. "Using native gel in two-dimensional PAGE for the detection of protein interactions in protein extract" J. Biochem. Biophys. Methods. 39, 143-151. (1999).*

* cited by examiner

*Primary Examiner*—Nam Nguyen
*Assistant Examiner*—Jeffrey Barton

(57) ABSTRACT

A multi-dimensional proteomic analysis method utilizing cationic electrophoresis is described. The method includes separating proteins in one direction using cationic electrophoresis and separating the proteins in a second orthogonal direction using other electrophoresis separation methods such as denaturing electrophoresis and electrophoresis subsequent to proteolytic cleavage or isofocussing. The two dimensional array may be used to determine various protein-protein interactions in a sample.

16 Claims, 1 Drawing Sheet

MULTI-DIMENSIONAL PROTEOMIC ANALYSIS METHOD

CROSS REFERENCE TO RELATED APPLICATION

This application is based on U.S. Provisional Application No. 60/279,125 filed on Mar. 28, 2001, herein incorporated by reference in its entirety.

BACKGROUND OF THE INVENTION

The complete set of proteins encoded by a genome of a given organism has been termed the proteome. Proteomics refers to the analysis of changes in the protein content of a cell, tissue, or body fluid associated with changes in physiological status. Such changes may be associated with development, changes in function, response to stimuli, the progression of disease, and the like.

The power of proteomics lies in the fact that processes within cells or complex organisms are controlled, modulated, and carried out by proteins. Therefore, two cell-physiological states, for example normal vs diseased, are represented by distinct protein profiles. Because of this, proteomics can be used, for example, to identify target molecules for therapeutics, to diagnose and track disease states, to investigate the molecular etiology of a disease, or to assess the effects of a therapeutic agent.

Proteomics addresses the composition of the set of proteins being expressed and the level of protein expression. Typically, proteins are first separated by iso-electric focusing, non-equilibrium pH gel electrophoresis (NEPHGE), or immobilized pH gradient (IPG) in a first dimension, and then by sodium dodecylsulfate polyacrylamide gel electrophoresis (SDS-PAGE) in a second dimension. Although such 2D PAGE methods are powerful techniques, there are two significant drawbacks to these approaches. First, protein complexes are disassembed during analysis. As a result, these existing methods do not detect sample differences related to protein:protein interactions or in the composition of multi-protein complexes. Second, due to the sigmoidal shape of log Mr vs. Rf plots, it is difficult to accurately assign Mr to proteins across a broad range of molecular weights.

It would be desirable to have a proteomic analysis method that allowed for easy determination of which peptides or proteins in a sample are associated with one another. The present invention provides a method to evaluate protein:protein interactions across a broad range of molecular weights.

SUMMARY OF THE INVENTION

An object of the present invention is to provide a proteomic analysis method that allows for the determination of which peptides or proteins in a sample are associated with one another.

A further object of the present invention is to provide a multi-dimensional proteomic analysis method that allows for the determination of which peptides or proteins in a sample are associated with one another.

Accordingly, the present invention is directed to multi-dimensional proteomic analysis method comprising the steps of separating a protein or peptide sample on a substrate by cationic electrophoresis in a first direction on the substrate, and separating the protein or peptide sample on the substrate by a second electrophoresis method in a second direction substantially orthogonal to the first direction to produce a two-dimensional array of separated proteins or peptides.

In one embodiment the cationic electrophoresis method may be performed first. In another embodiment, the second electrophoresis method may be selected from the group consisting of denaturing electrophoresis, electrophoresis subsequent to proteolytic cleavage, isoelectric focussing, NEPHGE, and IPG. The method may also include probing the array with antibodies and staining the array.

DETAILED DESCRIPTION OF THE INVENTION

The present invention is directed to an electrophoresis method that includes separating proteins or peptides using discontinuous cationic (CAT) electrophoresis in one direction on a substrate and separating proteins or peptides using another electrophoresis separation method substantially orthogonal to the separation from the discontinuous cationic electrophoresis. In this way a two-dimensional array of proteins or peptides is established on the substrate.

Figure 1A:
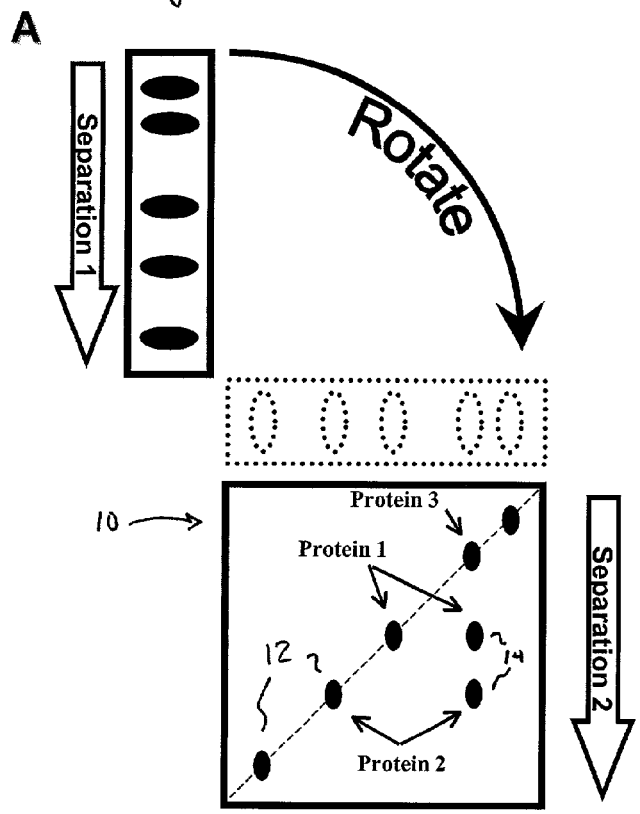
FIG. 1A depicts a two-dimensional array developed in accordance with one embodiment of the present invention illustrating the electrophoretic pattern expected in a normal sample in which two proteins bind together.
Figure 1B:
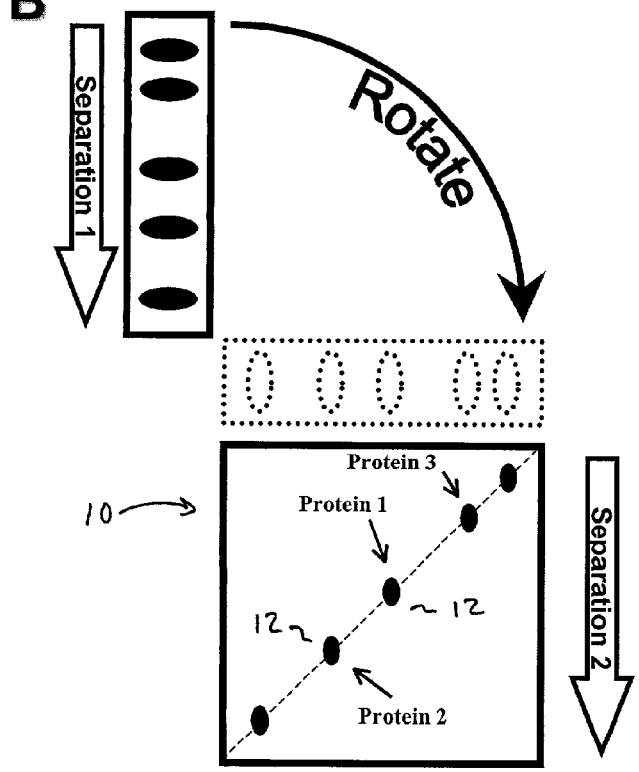
FIG. 1B depicts a two-dimensional array developed in accordance with another embodiment of the present invention illustrating the electrophoretic pattern expected in a diseased sample where the proteins do not bind with one another.

One example of the method of the present invention is to run non-denaturing CAT electrophoresis in the first dimension followed by denaturing gel electrophoresis in the second dimension. As shown in FIGS. 1A and 1B, the two-dimensional array 10 of proteins or peptides includes groups that appear on a diagonal 12 and groups that are off the diagonal 14. The groups located off the diagonal 14 represent proteins or peptides associated with one another, or, more generically, proteins that have their electrophoretic mobility altered in the second dimension relative to the first. For example, a nondenaturing separation followed by a denaturing separation in the second dimension may result in proteins migrating off the diagonal due to dramatic changes in conformation or charge to mass ratio of a moiety.

FIGS. 1A and 1B are diagrams of one embodiment of the invention applied to theoretical samples from normal and affected patient samples. These figures will now be described in conjunction with one embodiment of the present invention. This particular embodiment involves the solubilization and separation of protein samples using the CAT separation methodology described above, shown in the Figure as Separation 1. Following Separation 1, the samples in the gel are heat denatured in the presence of 2-mercaptoethanol. The gel is then rotated about 90 degrees such that Separation 2 is then carried out in a direction orthogonal to Separation 1. FIG. 1A illustrates the electrophoretic pattern expected in a normal sample in which two proteins, Protein 1 and Protein 2, bind together. This binding, for example, may be due to a post-translational modification of Protein 1, such that modified Protein 1 binds to Protein 2. As such, Protein 1 shows up in two distinct bands in the two-dimensional analysis: One band on the diagonal represents the unmodified and non-bound protein, and a second band off the diagonal represents the modified and bound moieties of Protein 1. Similarly, Protein 2 shows up as two bands: one bound and another non-bound.

FIG. 1B illustrates the electrophoretic pattern expected in a diseased sample in which, for example, Protein 1 does not undergo a post-translational modification. As such, Protein 1 does not bind Protein 2, and both Proteins 1 and 2 only run on the diagonal in the two-dimensional analysis.

To illustrate the utility of the approach a third protein, Protein 3, has been included in this example. Protein 3 runs at the same Mr as the combined Proteins 1 and 2 in the first dimension of the analysis. Because of this, and because a portion of Proteins 1 and 2 remain unbound under normal conditions, the differences in the two samples would be difficult to detect with a one dimensional analysis. Similarly, current proteomic analyses that depend on the use of SDS-PAGE would not be able to detect the difference between the samples. Since SDS-PAGE is carried out under denaturing conditions, Proteins 1 and 2 would be dissociated in both the normal and diseased samples prior to analysis.

The two-dimensional arrays produced in accordance with the method of the present invention may be used to diagnose the presence of disease, to assess the efficacy of a treatment, or to perform basic research.

As discussed above, one of the electrophoresis separation methods used in the present invention for separating proteins or peptides is the CAT electrophoresis separation method and is described in detail in U.S. Pat. No. 5,275,708 to Robert E. Akins, Jr. et al. (herein incorporated by reference in its entirety). Two of the attributes of this previously described system are that proteins are separated by log molecular weight across a much broader range of molecular weights than in typical "Laemmli" gels, and that certain protein:protein interactions and native structures are retained during the course of sample preparation and electrophoretic separation.

However, the CAT electrophoresis separation system when used alone does not address the generation of protein expression profiles in two-dimensional electrophoresis systems using non-denaturing polyacrylamide gel electrophoresis. Nor does the CAT electrophoresis separation system address the use of non-denaturing polyacrylamide gel electrophoresis technology in proteomic analysis.

The instant invention is based in part on the CAT electrophoretic separation methods and provides improvements thereto. The major improvements lie in three areas. First, multimeric protein structures are maintained. Second, an extended relationship between log Mr and Rf is made possible. Third, low Mr proteins are finely separated.

The present invention uses the CAT electrophoresis separation technology as a non-denaturing electrophoretic system in conjunction with other electrophoresis separation methods to generate two-dimensional electrophoretograms.

The discontinuous CAT electrophoresis separation method includes the use of a discontinuous polyacrylamide and agarose gel electrophoresis system that allows the fine separation of proteins based on molecular weight with the concomitant retention of native enzymatic activity. A cationic surfactant, such as cetyltrimethylammonium bromide (CTAB), is used and includes a stacking gel based on a zwitterion such as arginine, lysine, or glycine and a buffer such as tricine.

The charged, non-denaturing surfactants act as a solubilizing agent for proteins. Useful surfactants include, but are not limited to, cetyltrimethylammonium, tetradecyltrimethylammonium, decylsulfate, octylsulfate, and dodecylsulphonate. The surfactant binding imparts a constant charge to mass ratio among treated proteins, and forms protein complexes of uniform hydrodynamic shape. The selected surfactant may be included in both the sample and tank buffers.

The zwitterion acts as a high mobility current carrier in the tank buffer and acts as an agent to accomplish protein stacking due to low zwitterion mobility in the conditions of the stacking gel, and as a high mobility current carrier in the separator gel to allow efficient migration of stacked proteins.

The buffer may include, but is not limited to, Tricine, Hepes, MOPS, or Tris and is used to maintain the selected pH levels in the tank buffer, sample buffer, stacking gel, and separating gel, and to act as a counter ion for the carrying of current.

The CAT gel gives excellent separation of protein mixtures as tight, discrete bands, maintains native enzymatic activity in a number of sample proteins, and eliminates the extensive rinsing necessary to remove excess phosphate prior to phosphatase, ATPase, or calcium dependent assays in other systems.

The other electrophoresis separation methods that may used with the present invention may include electrophoresis methods known to those skilled in the art and include denaturing electrophoresis, electrophoresis subsequent to proteolytic cleavage, or isoelectric focussing, NEPHGE, IPG, or other separation technology know to those skilled in the art.

The other electrophoresis separation method would be carried out substantially orthogonal to the CAT electrophoresis separation. As discussed above, by separating the proteins or peptides in two substantially orthogonal directions, a two-dimensional array of separated proteins or peptides is created.

In one embodiment of the invention the CAT electrophoresis separation method would be used for the separation of native proteins, denatured proteins, or peptides in a first direction. After the conclusion of the CAT electrophoresis, the proteins or peptides are further separated in a second direction that is substantially orthogonal to the first direction by one of the other electrophoresis methods referenced above.

Alternatively, the proteins or peptides may be first separated by one of the other electrophoresis methods, such as denaturing electrophoresis, or electrophoresis subsequent to proteolytic cleavage, isoelectric focussing in one direction followed by further separation by CAT electrophoresis substantially orthogonal to the first separation.

In yet another embodiment of the present invention, CAT electrophoresis separation would be used for the separation of native proteins or denatured proteins in the first dimension of a multi-dimensional proteomic analysis. However, a second dimension would then be carried out in which denaturing electrophoresis, or electrophoresis subsequent to proteolytic cleavage, or isoelectric focussing, or other separation technology, would be carried out.

In one embodiment, the two electrophoresis separation methods are carried out sequentially. Once one electrophoresis separation method is completed the substrate or gel may be rotated about ninety degrees followed by the second electrophoresis separation method. Alternatively, the electrophoresis equipment could be configured such that orthogonal electrophoresis separation is obtained without rotation of the substrate.

In yet another embodiment of the present invention, CAT electrophoresis separation is used to separate proteins or peptides in one direction and used to further separate the proteins in a second, substantially orthogonal direction.

Once the two-dimension array of separated proteins or peptides is created, the resulting array could then be silver stained and densitometrically scanned to identify alterations in banding patterns between samples, for example between biopsies of normal versus diseased tissue. Arrays could also be probed with batteries of antibodies, lectins, toxins, nucleic acid probes, or other binding agents or stains. Arrays could be processed using proteolytic enzymes with the resulting fragments identified by mass spectrometry or amino acid analysis to identify and quantify protein or peptide bands.

The two-dimensional arrays of the present invention would allow investigators to rapidly assess differences in samples, for example blood cells, acquired from different sources, for example normal patients and affected patients, in terms of the protein:protein interactions present.

The differences in the two-dimensional profiles generated by the present invention would indicate the identities and quantities of proteins expressed (as in standard proteomic analysis), but, in addition, the proteomics analysis provided by the practice of the instant invention would also give information about protein:protein interactions and would allow a broader range of protein molecular weights, especially low molecular weights, to be evaluated at the same time.

A further example of the application of the two dimensional electrophoresis method would be the generation of databases associating the distribution of proteins in two dimensional electrophoretograms to the presence or absence of specific clinical symptoms, syndromes, or diseases. By incorporating the CAT electrophoresis separation method as one of the dimensions in a two-dimensional proteomic analysis, data regarding the interaction of proteins into complexes can be related to specific disease states. In this way, the present invention can be adapted to drug development, diagnostic, and research applications.

The present invention could be used in the generation of protein expression profiles for the evaluation of transcription factors. Transcription factors are nucleic acid binding proteins that modulate gene expression. A specific transcription factor may have different effects on gene expression depending on its association with other proteins in complexes. The CAT electrophoresis separation methods identify changes in the size of such complexes. By performing the CAT electrophoresis the first dimension of an analysis and denaturing gel electrophoresis as a second dimension, the identify the proteins that make up the different complexes would be revealed as well as identify other protein:protein interactions or other peptide:peptide interactions.

The invention will be illustrated further in the following examples. The examples are provided to illustrate various aspects of the present invention and not intended to limit the present invention in any way.

EXAMPLE 1

Tissue biopsy samples are collected from a group of patients afflicted with a particular condition and from a group of control individuals who are not affected. Each sample is handled separately as follows.

1) Tissue samples are finely minced and rinsed with physiological saline. Five mg of the minced material is solubilized in 1 ml of sample buffer (10 mM Tricine-Na, (pH 8.8) with 1% cetyltrimethylammonium bromide (CTAB), and 10% glycerol).
2) The sample is spun at 16,000× g for 30 sec to remove insoluble material.
3) The supernatant is loaded onto a 80 mm×90 mm×0.8 mm discontinuous CTAB-Arginine-Tricine (CAT) polyacrylamide gel, which is prepared as follows:
    1) A stock of acrylamide (prepared by combining 38.93 g of ultrapure acrylamide with 1.07 g of bis-acrylamide in a volume of distilled water to equal 100 ml total) is used to make an 6% T separating gel in 375 mM Tricine-Na (pH 7.96).
    2) A stacking gel of 0.7% agarose in 125 mM Tricine-Na (pH 9.96) with 0.1% CTAB is poured on top of the separating gel.
    3) A running buffer (25 mM Tricine-14 mM arginine, pH 8.2, with 0.1% CTAB) is placed in contact with the top of the stacking gel and the bottom of the separating gel.
4) A voltage (100 V) is placed across the gel system. When the salt front reaches the separating gel, the voltage is raised to 150 V until the salt front reaches the bottom of the gel (approximately 45 minutes).
5) The gel is disassembled, and a longitudinal strip containing the separated sample is cut from the gel. The strip is placed into a denaturing solution containing 125 mM Tricine-Na (pH 9.96), 0.1% CTAB, and 2% β-mercaptoethanol. The strip is heated to 95 degrees Celsius, allowed to cool and placed directly on top of a second separating gel, which is composed of 6% T acrylamide in 375 mM Tricine-Na (pH 7.96). Running buffer is placed as before.
6) A voltage (100 V) is placed across the gel system. When the salt front reaches the separating gel, the voltage is raised to 150 V until the salt front reaches the bottom of the gel (approximately 45 minutes).
7) The gel is removed from the apparatus and stained for total protein using a commercially available silver stain preparation (for example, Silver-Stain-Plus from Bio-Rad).

The location and relative staining of protein bands are compared within the group of control and patient samples to indicate variability within the groups. The consensus staining patterns for each group are then compared to reveal changes related to the disease. In general, proteins that do not associate into multi-protein aggregates in the first dimension will appear along the diagonal axis of the final gel. Proteins that do associate in aggregates will appear off the diagonal and will be resolved into multiple bands in the direction of the second electrophoresis based on the Mr of each protein in the grouping. Using this methodology, changes in the interaction of proteins can be evaluated as they relate to the disease status of the patient.

EXAMPLE 2

As in the previous example, tissue biopsy samples are collected from a group of patients afflicted with a particular condition and from a group of control individuals who are not affected. Each sample is handled separately, and the first dimension (steps 1 through 4) is carried out as in Example 1. Thereafter, each sample is processed as follows.

1) The gel is disassembled, and a longitudinal strip containing the separated sample is cut from the gel. The strip is placed into a denaturing solution containing 125 mM Tricine-Na (pH 9.96), 0.1% CTAB, and 2% β-mercaptoethanol. The strip is heated to 95 degrees Celsius, allowed to cool and placed directly on top of a second separating gel, which is composed of 10% T acrylamide in 375 mM Tricine-Na (pH 7.96). Running buffer is placed as before. A solution of protease containing 10 micrograms per milliliter trypsin in 125 mM Tricine (pH 9.96) with 0.1%

CTAB, 10% glycerol, and 0.001% bromphenol blue (BPB) is placed through the running buffer directly on top of the gel strip.
2) A voltage (100 V) is placed across the gel system. When the BPB dye front reaches the separating gel, the voltage is turned off for 30 minutes to allow proteolytic digestion to occur.
3) The voltage is set to 150 V, and the samples separated until the BPB dye front reaches the bottom of the gel (approximately 1 hour).
4) The gel is removed from the apparatus and stained for total protein using a commercially available silver stain preparation (for example, Silver-Stain-Plus from Bio-Rad).

The location and relative staining of peptide bands are compared within the group of control and patient samples to indicate variability within the groups. The consensus staining patterns for each group are then compared to reveal changes related to the disease. In general, individual proteins exhibit charateristic proteolytic banding patterns, and the presence of similar banding patterns at different points along the first dimension suggest the presence of the same protein.

EXAMPLE 3

As in the previous two examples, tissue biopsy samples are collected from a group of patients afflicted with a particular condition and from a group of control individuals who are not affected. Each sample is handled separately, and the first dimension and second dimensions (steps 1 through 6) are carried out as in Example 1. Thereafter, each sample is processed as follows, similar to Example 2.
1) The gel is disassembled, and using a gel prepared in parallel and stained as a reference, a longitudinal strip containing the separated sample is cut from the gel. For example, this strip would contain bands that migrate off the principal diagonal of the gel. The strip is placed into a denaturing solution containing 125 mM Tricine-Na (pH 9.96), 0.1% CTAB, and 2% β-mercaptoethanol. The strip is heated to 95 degrees Celsius, allowed to cool and placed directly on top of a second separating gel, which is composed of 10% T acrylamide in 375 mM Tricine-Na (pH 7.96). Running buffer is placed as before. A solution of protease containing 10 micrograms per milliliter trypsin in 125 mM Tricine (pH 9.96) with 0.1% CTAB, 10% glycerol, and 0.001% bromphenol blue (BPB) is placed through the running buffer directly on top of the gel strip.
2) A voltage (100 V) is placed across the gel system. When the BPB dye front reaches the separating gel, the voltage is turned off for 30 minutes to allow proteolytic digestion to occur.
3) The voltage is set to 150 V, and the samples separated until the BPB dye front reaches the bottom of the gel (approximately 1 hour).
4) The gel is removed from the apparatus and stained for total protein using a commercially available silver stain preparation (for example, Silver-Stain-Plus from Bio-Rad).

The location and relative staining of peptide bands are compared within the group of control and patient samples to indicate variability within the groups. The consensus staining patterns for each group are then compared to reveal changes related to the disease. By comparing peptide maps generated from bands taken from different regions of the gel, samples can be analysed to determine the presence of the same protein in multiple protein complexes.

EXAMPLE 4

As in the previous three examples, tissue biopsy samples are collected from a group of patients afflicted with a particular condition and from a group of control individuals who are not affected. Each sample is handled separately as follows.
1) Tissue samples are finely minced and rinsed with physiological saline. Ten mg of the minced material is solubilized in 2 ml of IPG hydration buffer (6M urea, 0.1% dithiothreitol, 0.5% v/v Pharmalyte 3-10 [Amersham_Pharmacia Biotech], 1.25 mM acetic acid, and 0.5% Triton X-100 nonionic surfactant).
2) The sample is spun at 16,000× g for 30 sec to remove insoluble material.
3) The supernatant is placed onto a dehydrated ReadyStrip IPG strip (BioRad) overnight at 4 degrees Celsius.
4) The sample on the IPG strip is electrophoresed to completion in PROTEAN IEF cell (BioRad), then the electrophoresed IPG strip is equilibrated with CAT buffer (125 mM Tricine-Na (pH 9.96), 0.1% CTAB, and 2% β-mercaptoethanol) and loaded onto a 80 mm×90 mm×0.8 mm discontinuous CTAB-Arginine-Tricine (CAT) polyacrylamide gel, which is prepared as follows:
  1) A stock of acrylamide (prepared by combining 38.93 g of ultrapure acrylamide with 1.07 g of bis-acrylamide in a volume of distilled water to equal 100 ml total) is used to make an 6% T separating gel in 375 mM Tricine-Na (pH 7.96).
  2) The IPG strip is placed onto the separating gel.
  3) A stacking gel of 0.7% agarose in 125 mM Tricine-Na (pH 9.96) with 0.1% CTAB is poured on top of the IPG strip and separating gel.
  4) A running buffer (25 mM Tricine-14 mM arginine, pH 8.2, with 0.1% CTAB) is placed in contact with the top of the stacking gel and the bottom of the separating gel.
  5) A voltage (100 V) is placed across the gel system. When the salt front reaches the separating gel, the voltage is raised to 150 V until the salt front reaches the bottom of the gel (approximately 45 minutes).
  6) The gel is removed from the apparatus and stained for total protein using a commercially available silver stain preparation (for example, Silver-Stain-Plus from Bio-Rad).

The location and relative staining of protein bands are compared within the group of control and patient samples to indicate variability within the groups. The consensus staining patterns for each group are then compared to reveal changes related to the disease. In general, proteins will separate in a manner similar to standard 2D-PAGE except that the log Mr vs Rf relationship of proteins separated in the second dimension will be linear across a much broader range, and, importantly, low Mr proteins will be more distinctly separated. These improvements over SDS-based 2D-PAGE provide better resolution of bands and more uniformity across multiple preparations. Using this methodology, changes in the interaction of proteins can be evaluated as they relate to the disease status of the patient.

It will be readily understood by those persons skilled in the art that the present invention is susceptible to broad utility and application. Many embodiments and adaptations of the present invention other than those herein described, as well as many variations, modifications and equivalent arrangement, will be apparent from or reasonably suggested by the present invention and the foregoing description without departing from the substance or scope of the present invention.

Accordingly, while the present invention has been described in detail in relation to its preferred embodiment, it is to be understood that this disclosure is only illustrative and exemplary of the present invention and is made merely for purposes of providing a full and enabling disclosure of the invention. The foregoing disclosure is not intended to be construed to limit the present invention or otherwise exclude any other embodiments, adaptations, variations, modifications or equivalent arrangements, the present invention being limited only by the claims and the equivalents thereof.

What is claimed is:

1. A method for generating a two-dimensional protein expression profile for determining protein: protein interactions in a sample said method comprising the steps of:
    separating a non-denatured protein sample in a first dimension by a non-denaturing cationic (CAT) gel electrophoresis that retains protein: protein interactions during the non-denaturing electrophoretic separation;
    denaturing the separated proteins in the non-denatured gel to produce denatured proteins; and
    separating the denatured proteins by a denaturing gel electrophoresis in a second dimension substantially orthogonal to the first dimension using denaturing CAT electrophoresis following the non-denaturing CAT electrophoresis used in the first dimension to produce a two-dimensional protein expression profile having a plurality of protein bands positioned substantially along a diagonal axis relative to the first dimension and the second dimension, each band representing one or more unbound proteins, with any proteins forming multi-protein aggregates with the unbound proteins appearing as one or more bands in positions offset from the diagonally positioned bands, with the offset positions defining a grouping corresponding to the molecular weight of each diagonally positioned protein band.

2. The method of claim 1, further comprising the step of analyzing said two-dimensional protein expression profile for the presence of said protein: protein interactions.

3. The method of claim 1, wherein the first dimension CAT gel is a discontinuous gel having a first stacking portion and a second separating portion.

4. The method of claim 3, wherein the stacking portion of the CAT gel includes one or more zwitterions selected from group consisting of arginine, lysine, glycine and a combination thereof.

5. The method of claim 1, further comprising the step of staining the two-dimensional gel.

6. The method of claim 5, wherein the stain is selected from the group consisting of silver stain, Coomassie blue stain and Cypro dyes.

7. The method of claim 1, further comprising the step of probing the two-dimensional gel for a protein of interest with a compound selected from the group consisting of an antibody, a lectin, a toxin, and a nucleic acid probe.

8. The method of claim 1, wherein said denaturing step comprises the steps of:
    placing the gel in a denaturing solution; and
    heat-treating the gel at about 95° C.

9. A method for generating a two-dimensional peptide expression profile for determining peptide: peptide interactions in a sample, comprising the steps of:
    separating a non-denatured peptide sample in a first dimension by non-denaturing cationic (CAT) gel electrophoresis such that said peptide: peptide interactions are retained during the non-denaturing electrophoretic separation;
    denaturing the separated peptides in the non-denatured gel to produce denatured peptides, and
    separating the denatured peptides by a denaturing gel electrophoresis in a second dimension substantially orthogonal to the first dimension using denaturing CAT electrophoresis following the non-denaturing CAT electrophoresis used in the first dimension to produce a two-dimensional peptide expression profile having a plurality of peptide bands positioned substantially along a diagonal axis relative to the first dimension and the second dimension, each band representing one or more unbound peptides, with any peptides forming multi-peptide aggregates with the unbound peptides appearing as one or more bands in positions offset from the diagonally positioned bands, with the offset positions defining a grouping corresponding to the molecular weight of each diagonally positioned peptide band.

10. The method of claim 9, further comprising the step of analyzing said two-dimensional peptide expression profile for the presence of said peptide: peptide interactions.

11. The method of claim 9, wherein the first dimension CAT gel is a discontinuous gel having a first stacking portion and a second separating portion.

12. The method of claim 11, wherein the stacking portion of the CAT gel includes one or more zwitterions selected from the group consisting of lysine, arginine, glycine and a combination thereof.

13. The method of claim 9, further comprising the step of staining the two-dimensional gel.

14. The method of claim 13, wherein the stain is selected from the group consisting of silver stain, Coomassie blue stain, and Cypro dyes.

15. The method of claim 9, further comprising the step of probing the two-dimensional gel for a peptide of interest with a compound selected from the group consisting of an antibody, a lectin, a toxin, and a nucleic acid probe.

16. The method of claim 9, wherein said denaturing step comprises the steps of:
    placing the gel in a denaturing solution; and
    heat-treating the gel at about 95° C.

* * * * *